(12) United States Patent  
Hale et al.

(10) Patent No.: US 6,663,559 B2
(45) Date of Patent: Dec. 16, 2003

(54) INTERFACE FOR A VARIABLE DIRECTION OF VIEW ENDOSCOPE

(75) Inventors: Eric L. Hale, South Pasadena, CA (US); Nathan J. Schara, Pasadena, CA (US); Hans D. Høeg, Arcadia, CA (US)

(73) Assignee: EndActive, Inc., Arcadia, CA (US)

( * ) Notice: Subject to any disclaimer, the term of this patent is extended or adjusted under 35 U.S.C. 154(b) by 166 days.

(21) Appl. No.: 10/020,374

(22) Filed: Dec. 14, 2001

(65) Prior Publication Data

US 2003/0114730 A1 Jun. 19, 2003

(51) Int. Cl.⁷ .................................................. A61B 1/04
(52) U.S. Cl. ........................................ 600/118; 600/173
(58) Field of Search ................................. 600/173, 117, 600/118, 109; 606/130; 348/65, 74

(56) References Cited

U.S. PATENT DOCUMENTS

| | | | |
|---|---|---|---|
| 4,697,577 A | * | 10/1987 | Forkner ...................... 600/173 |
| 5,313,306 A | | 5/1994 | Kuban |
| 5,524,180 A | | 6/1996 | Wang |
| 5,776,050 A | * | 7/1998 | Chen et al. .................. 600/117 |
| 5,876,325 A | * | 3/1999 | Mizuno et al. ............. 600/102 |
| 5,907,664 A | | 5/1999 | Wang |
| 5,954,634 A | | 9/1999 | Igarashi |
| 6,097,423 A | | 8/2000 | Mattsson-Boze |
| 6,371,909 B1 | * | 4/2002 | Hoeg et al. .................. 600/173 |
| 6,428,470 B1 | * | 8/2002 | Thompson ................... 600/173 |

* cited by examiner

*Primary Examiner*—John P. Leubecker
(74) *Attorney, Agent, or Firm*—Morrison & Foerster

(57) ABSTRACT

An interface for a variable direction of view endoscope having an input device for receiving commands from the user, an output device for adjusting the endoscope, and an electronic processing device to determine the appropriate output based on the given input. The processing device may be configured to allow operation assisting features including a coordinate system aligned with the current view, a coordinate system aligned with the user's surroundings, a coordinate system aligned with the operating cavity, a memory to facilitate the immediate return to a user selected direction of view, and a clear indication of the current direction of view.

25 Claims, 9 Drawing Sheets

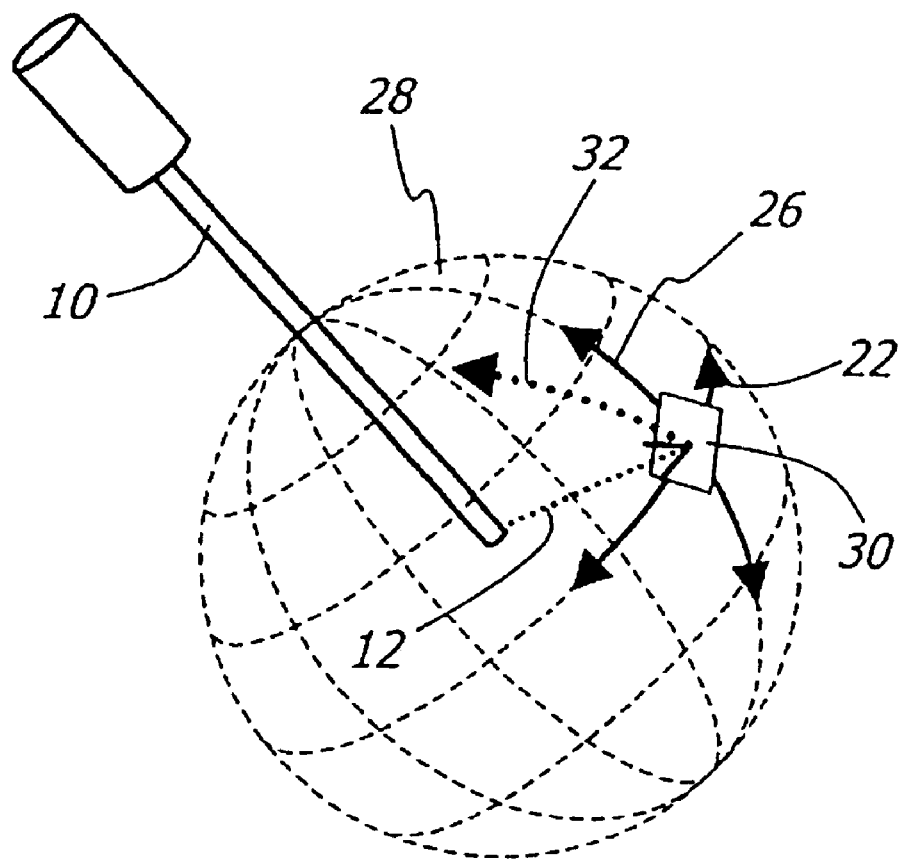

Prior Art

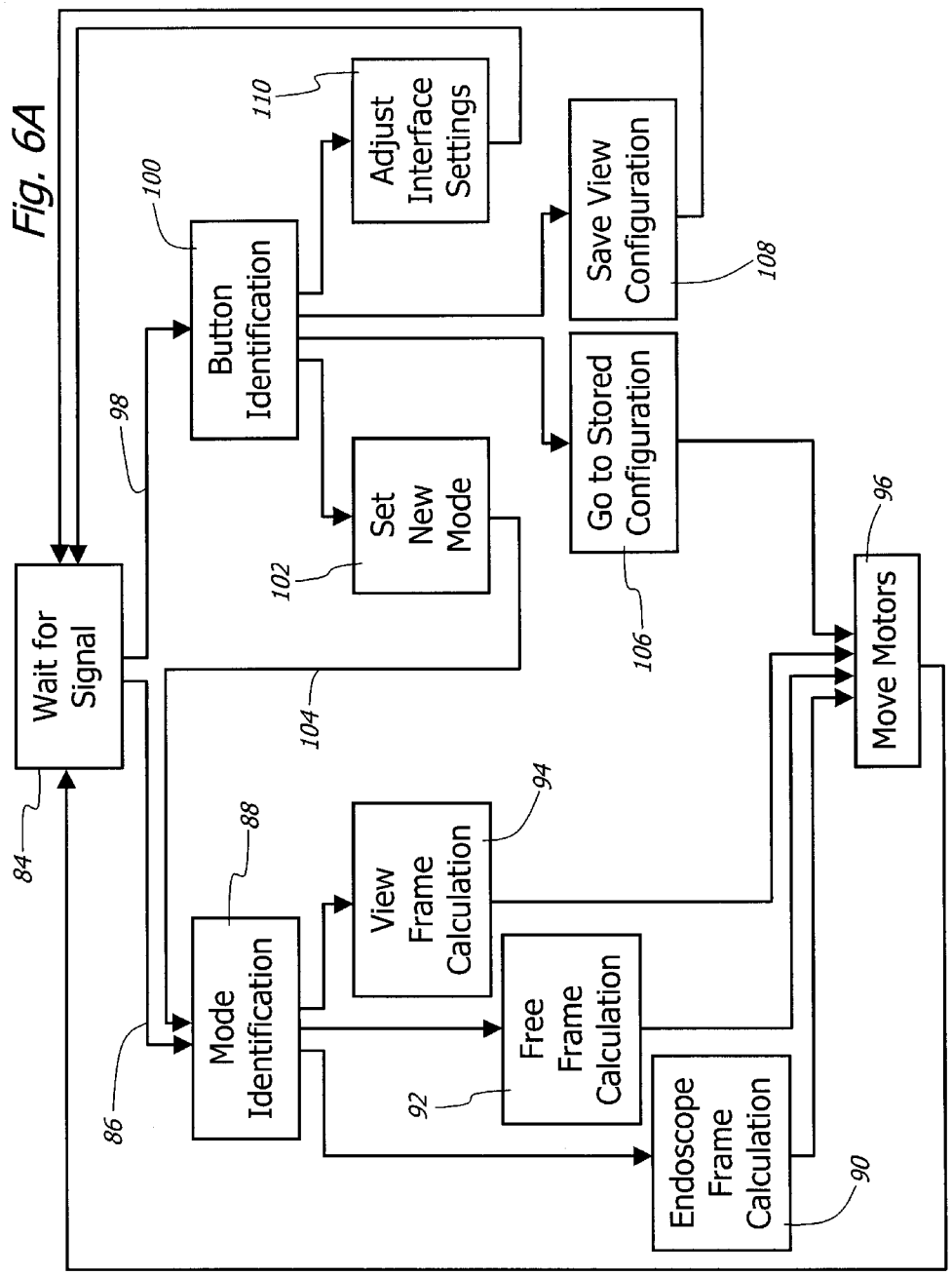

INTERFACE FOR A VARIABLE DIRECTION OF VIEW ENDOSCOPE

FIELD OF THE INVENTION

The present invention relates to endoscopes (including devices such as borescopes, fiberscopes, etc.) and specifically to control of endoscopes capable of varying their direction of view.

BACKGROUND OF THE INVENTION

Endoscopes are elongated devices used to visualize the insides of cavities. Recent developments have brought about endoscopes capable of varying their direction of view. The purpose of these endoscopes is to allow the user to scan over a larger area with less device movement than traditional endoscopes and provide greater flexibility in obtaining a desired view.

Most endoscopes capable of varying their direction of view include mechanically steered optical components. These are controlled using one or more knobs or similar devices for adjusting the degrees of freedom available in the endoscope along the respective axis of each degree. Examples of these are disclosed in U.S. Pat. No. 3,880,148 to Kanehira et al. (1975), U.S. Pat. No. 4,697,577 to Forkner (1987), U.S. Pat. No. 3,572,325 to Bazell et al. (1971), and WIPO publication WO 99/42028 by Høeg et al. (1999). In all of these examples, each axis of adjustment is controlled independently. Making a desired compound adjustment involving two or more axes is difficult to accomplish, requiring multiple hands and/or great dexterity.

Other endoscopes capable of varying their direction of view include those disclosed in U.S. Pat. No. 5,954,634 to Igarashi (1998) and U.S. Pat. No. 5,313,306 to Kuban, et al. (1994). These devices provide a viewed area variably selected from within a wide-angle captured image giving a result similar to those with mechanically adjusted optical components. Like mechanically adjusted variable direction of view endoscopes, these devices may only be adjusted in a predetermined manner with predetermined axes.

Each of the above endoscopes has a set of adjustment axes that define a natural coordinate system for that endoscope. In the natural coordinate system, each degree of freedom of the endoscope is one axis of the coordinate system. Each endoscope is controlled in relation to its natural coordinate system. Due to differences in the design of varying endoscopes, each endoscope's natural coordinate system may be different. This can create a significant problem for users when attempting to work with a different endoscope than that which they are accustomed to. The natural coordinate system of an endoscope is always aligned with that endoscope rather than with the user's surroundings or the operating cavity. The user can become confused when trying to selectively scan within a coordinate system that fails to align with a familiar environment.

Because the distal end of a variable direction of view endoscope is generally not visible during use, the user often requires an external indication of the current viewing direction. Some endoscopes fail to have any method of indicating the direction of view, while others include indicators that are inconvenient or difficult for the user to interpret. Not knowing the current direction of view makes it challenging to adjust to a desired direction of view or find a particular feature within the cavity. Additionally, returning to a previous direction of view can be quite challenging.

Although prior art variable direction of view endoscopes may have been designed for easy and efficient use, the interfaces heretofore known suffer from at least the following disadvantages:

a. The interface provided with each endoscope can be unintuitive and confusing for the user.

b. The disjoint control of multiple degrees of freedom makes precision compound adjustments prohibitively difficult to execute.

c. Various types of variable direction of view endoscopes require very different methods of operation.

d. The coordinate system available can not usually be aligned with the user's surroundings.

e. The coordinate system available can not usually be aligned with the operating cavity.

f. The current direction of view can be difficult to determine.

g. The user must manually adjust the endoscope to return to a particular direction of view.

Some endoscopic control systems include actuators such as motors to assist the user in controlling the view. For example, U.S. Pat. No. 5,524,180 to Wang et al. (1996) discloses a motorized control system for automated positioning of an endoscope. Such control systems utilize a computer and robotic arm to control the movement of an endoscope for the purpose of changing the viewing direction. However, instead of moving the entire endoscope, variable direction of view endoscopes should be controlled in a way that utilizes their internal direction of view adjustment systems. Therefore, existing electro-mechanical endoscope control systems are not well suited to situations in which the use of a variable direction of view endoscope is desired.

Accordingly, the primary object of the present invention is to provide an easy-to-use interface for a variable direction of view endoscope capable of adjusting multiple degrees of freedom of the endoscope simultaneously to execute precision compound adjustments. Another object of the present invention is to use this interface to mask the specific implementation of the endoscope from the user through a standard set of displays and controls. Yet another object of the present invention is to provide an interface having several different control coordinate systems for the user to choose between, enabling more efficient and effective procedures.

Still further objects and advantages will become apparent from the ensuing description and drawings.

BRIEF SUMMARY OF THE INVENTION

In accordance with the present invention, an interface for a variable direction of view endoscope comprises an input means for receiving commands from the user, an output means for adjusting the endoscope, and an electronic processing device to determine the appropriate output based on the given input. In certain embodiments, the processing device may be configured to allow operation-assisting features including:

a. a control coordinate system aligned with the endoscope;

b. a control coordinate system aligned with the current view;

c. a control coordinate system aligned with the user's surroundings;

d. a control coordinate system aligned with the operating cavity;

e. a clear display of one or more coordinate systems;

f. a memory to facilitate the immediate return to a user selected direction of view; and g. a clear indication of the current direction of view.

The term "endoscope" as used herein is defined as an endoscope (used for medical procedures) or any similar device such as a borescope, a fiberscope, etc. The term "endoscope configuration" used herein is defined as a set comprised of an orientation (or state) of each axis (or degree of freedom) of a endoscope. The term "control coordinate system" is defined as the coordinate system with respect to which control inputs are made and interpreted. The term "natural coordinate system of an endoscope" is defined as a coordinate system defined by the adjustment axes of an endoscope and may be used to parameterize a viewing direction and orientation with respect to the normal operation of that endoscope. The term "current view coordinate system" is defined as a coordinate system which is always aligned with the current viewing direction and orientation. An arbitrary coordinate system may be any other coordinate system related to the endoscope.

What is claimed is an interface for use with a variable direction of view endoscope, wherein a distal portion of said endoscope is disposed within a cavity, comprising an input means for receiving commands from a user, a tracking means for providing view vector orientation information, a processing means for receiving said commands and said orientation information and performing operations, comprising the calculation of a coordinate system that can change in alignment with said endoscope, and a viewing means for providing a current endoscopic view.

BRIEF DESCRIPTION OF THE DRAWINGS

FIGS. 1A, 1B, and 1C diagram the basic operational characteristics of the prior art.

FIGS. 6A and 6B are flow charts illustrating the operation of the central control unit according to two embodiments of the invention.

DETAILED DESCRIPTION OF THE INVENTION

The following detailed description illustrates the invention by way of example, not by way of limitation of the principles of the invention. This description will clearly enable one skilled in the art to make and use the invention, and describes several embodiments, adaptations, variations, alternatives and uses of the invention, including what we presently believe is the best mode of carrying out the invention.

Figure 1A:
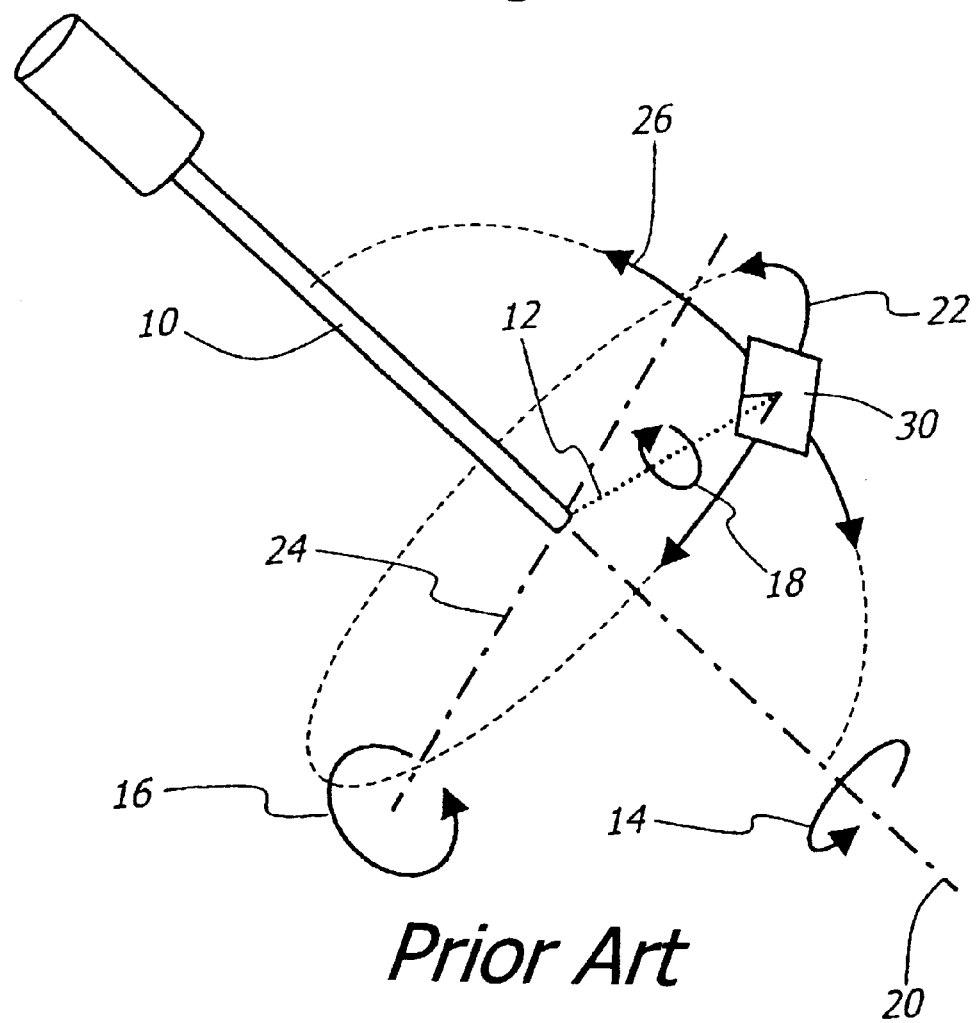

FIG. 1A is a diagram of a basic variable direction of view endoscope 10. Such an endoscope typically has a view vector 12 with at least two degrees of freedom 14, 16. The first degree of freedom 14 permits rotation of the view vector 12 about the longitudinal axis of the endoscope 20, which allows the view vector 12 to scan in a latitudinal direction 22. The second degree of freedom 16 permits rotation of the view vector 12 about an axis 24 perpendicular to the longitudinal axis 20, which allows the view vector 12 to scan in a longitudinal direction 26. These degrees of freedom define a natural endoscope coordinate system 28 as shown in FIG. 1B.

A third degree of freedom 18 may also be available because it is usually possible to adjust the rotational orientation of the endoscopic view 30. This is frequently accomplished by simply rotating an imaging device, such a camera, which is coupled to the proximal end of the endoscope. View rotation may also be provided using a prism built into the endoscope or by digitally rotating the image before viewing. Regardless of the method used, the view vector 12 is considered the axis of rotation for the view 30.

Figure 1C:
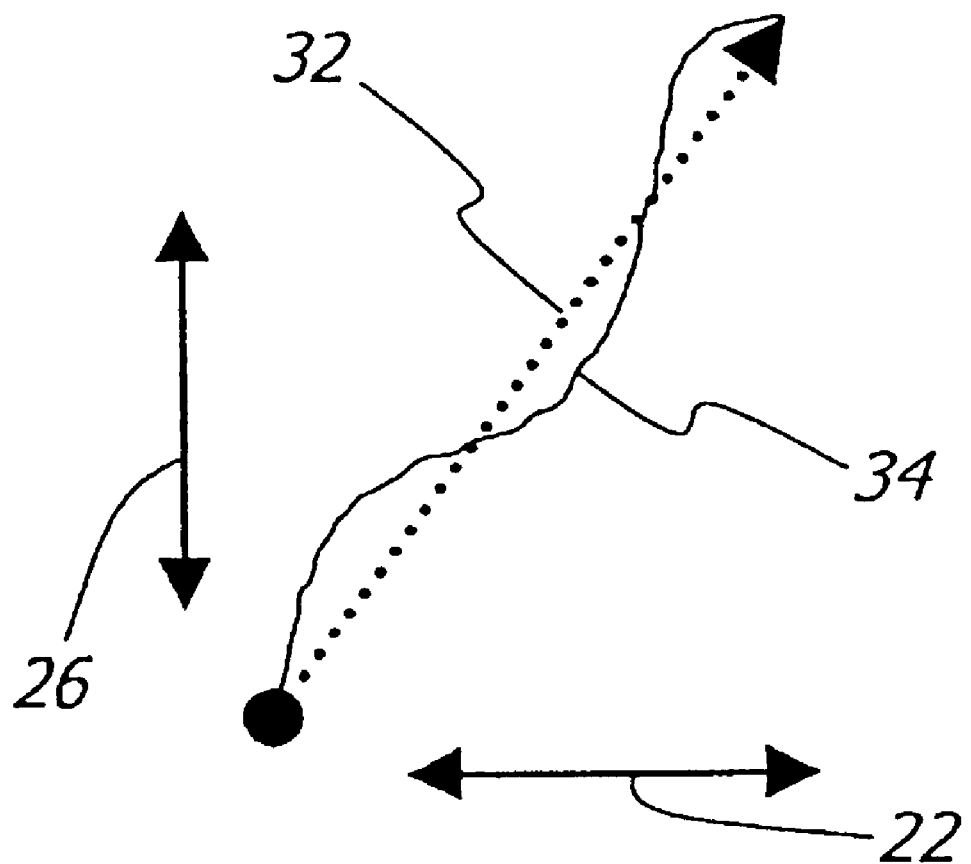

A user typically controls the view by adjusting the first degree of freedom 14 and second degree of freedom 16 to select a desired direction for the view vector 12. The axes may be adjusted separately or at the same time. Once the desired direction has been obtained, the rotational orientation of the resulting image is adjusted as desired. However, because each adjustment axis is controlled independently, scanning along an arbitrary path 32 that does not line up with either of the principal scanning directions 22, 26 is not easily accomplished. This discrepancy is demonstrated in FIG. 1C which depicts a typical path 34 traced by the view vector 12 of a traditional variable direction of view endoscope 10 while attempting to achieve the desired scan path 32. The foregoing scenario can readily be likened to the challenging problem of trying to appropriately adjust the two knobs of an Etch-A-Sketch®, described in U.S. Pat. No. 3,760,505 to Clark, in order to draw a desired diagonal line or curve. Moreover, when the rotational orientation of the view is adjusted, changing the apparent directions of the axes, this problem is worsened.

Figure 2:
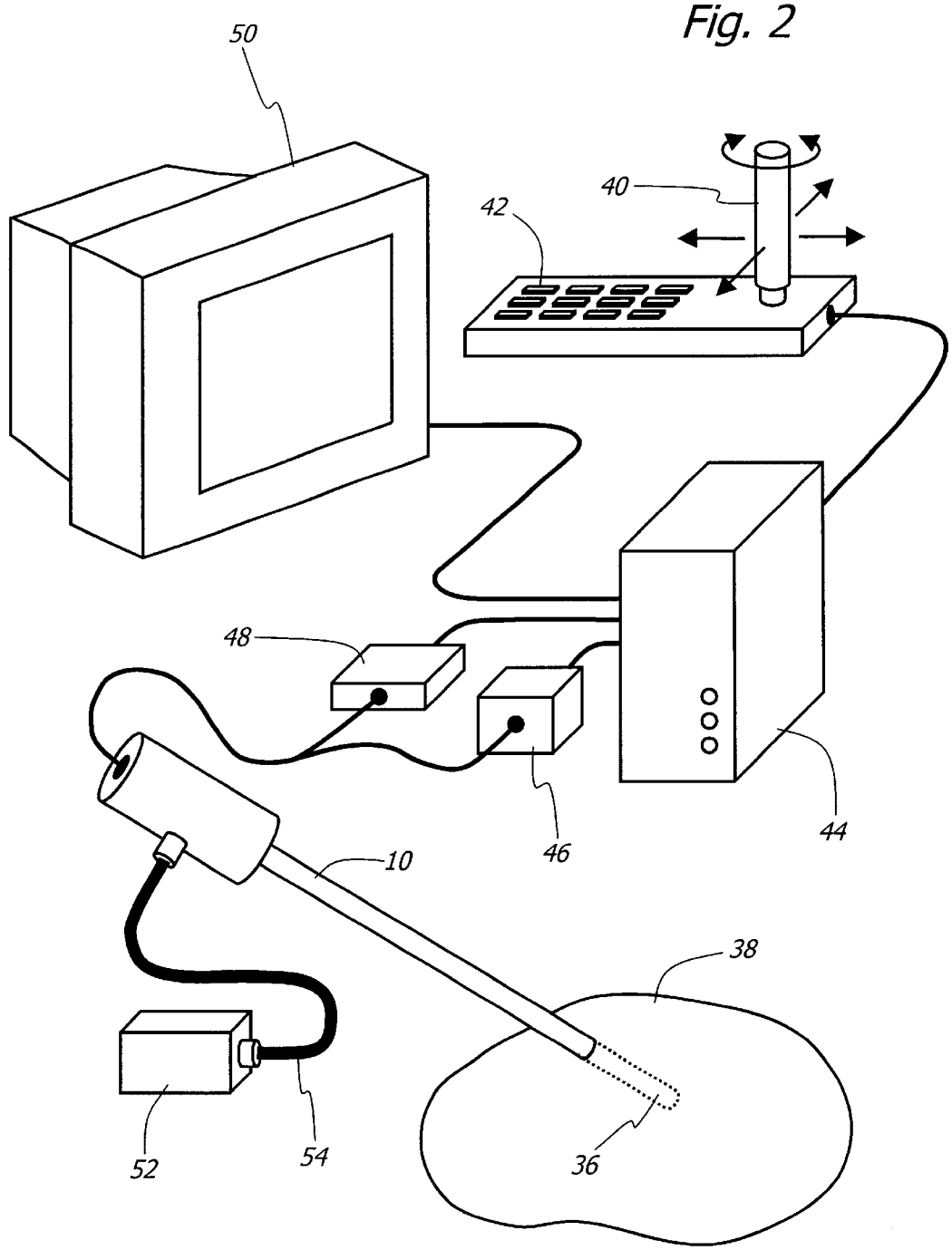
FIG. 2 is an illustration of a complete endoscopic operating system according to the preferred embodiment of the invention.

A preferred embodiment of a complete endoscopic viewing system, including the interface system of the present invention, is described herein with reference to FIG. 2. A variable direction of view endoscope 10, similar to the one shown in FIG. 1A, is positioned with its distal end portion 36 in a cavity to be examined 38. The endoscope is equipped with small motors (not shown) that enable electronic control of each degree of freedom of the endoscope, and encoders (not shown) that provide information about of the current orientation of the view about each respective axis. The motors and encoders permit each axis to be parameterized as a variable with a value ranging from −180 degrees to +180 degrees. The following variables are provided in the interface system for storing the encoder values corresponding to the current endoscope configuration:

$\theta_C$=the angle of the view vector about the longitudinal axis of the endoscope (first degree of freedom).

$\phi_C$=the angle of the view vector about the axis perpendicular to the longitudinal axis (second degree of freedom).

$\zeta_C$=the angle of the arbitrary rotational orientation of the view (third degree of freedom).

A three-axis joystick 40 gives a user right/left, up/down, and counter-clockwise/clockwise input capabilities. These inputs can be stored as +/−X, +/−Y, and +/−Z, respectively. A keypad 42 facilitates additional input. The input is received by a central control unit 44. The central control unit 44, a computer in the preferred embodiment, processes input from the user and information from the endoscope encoders to establish an appropriate adjustment for each axis. The appropriate adjustment is based on a control coordinate system and may be dependent upon previous inputs, adjustments, and endoscope configurations. The following variables are provided in the interface system for storing the encoder values corresponding to the desired endoscope configuration:

$\theta_D$=the desired angle of the view vector about the longitudinal axis of the endoscope (first degree of freedom).

$\phi_D$=the desired angle of the view vector about the axis perpendicular to the longitudinal axis (second degree of freedom).

$\zeta_D$=the desired angle of the arbitrary rotational orientation of the view (third degree of freedom).

Once the appropriate adjustment has been calculated, the adjustment information is provided to a motor control unit 46 as $\theta_D$, $\phi_D$, and $\zeta_D$. The motor control unit 46 controls the endoscope configuration through the motors in the endoscope 10. Specifically, the motor control unit 46 adjusts the endoscope until $\theta_C$, $\phi_C$, and $\zeta_C$ are equal to $\theta_D$, $\phi_D$, and $\zeta_D$. Upon the completion of the adjustment, the interface system is ready for another input. By making numerous small adjustments in rapid succession, the user is given the impression of smooth, continuous adjustment. An image acquisition unit 48 receives image signals from the endoscope 10 and adjusts the signals as needed. The central control unit 44 receives the adjusted signals from the image acquisition unit 48. An endoscopic video image and additional relevant information are relayed to a video display device 50 for presentation to the user. Illumination for the cavity 38 is delivered through the endoscope 10 from a standard light source 52 via a standard light guide 54.

In the preferred embodiment, various modes of operation are provided for the user. A first mode of operation can be thought of as an endoscope-frame mode. In this mode, the control coordinate system is equivalent to the natural coordinate system of the endoscope. Inputs from the user are directly applied to the endoscope configuration. The X value from the joystick is added to $\theta_C$ to provide $\theta_D$. The Y value from the joystick is added to $\phi_C$ to provide $\phi_D$. The Z value from the joystick is added to $\zeta_C$ to provide $\zeta_D$. Endoscope-frame mode is very similar to the standard operation of a variable direction of view endoscope. Although operation of the endoscope is still limited to the natural coordinate system of the endoscope, easily specified compound adjustments can be precisely carried out by the interface system. However, in this mode it may still be difficult for a user to determine his or her desired adjustment as the orientation of each axis of motion is not constant relative to the endoscopic view.

Figure 3:
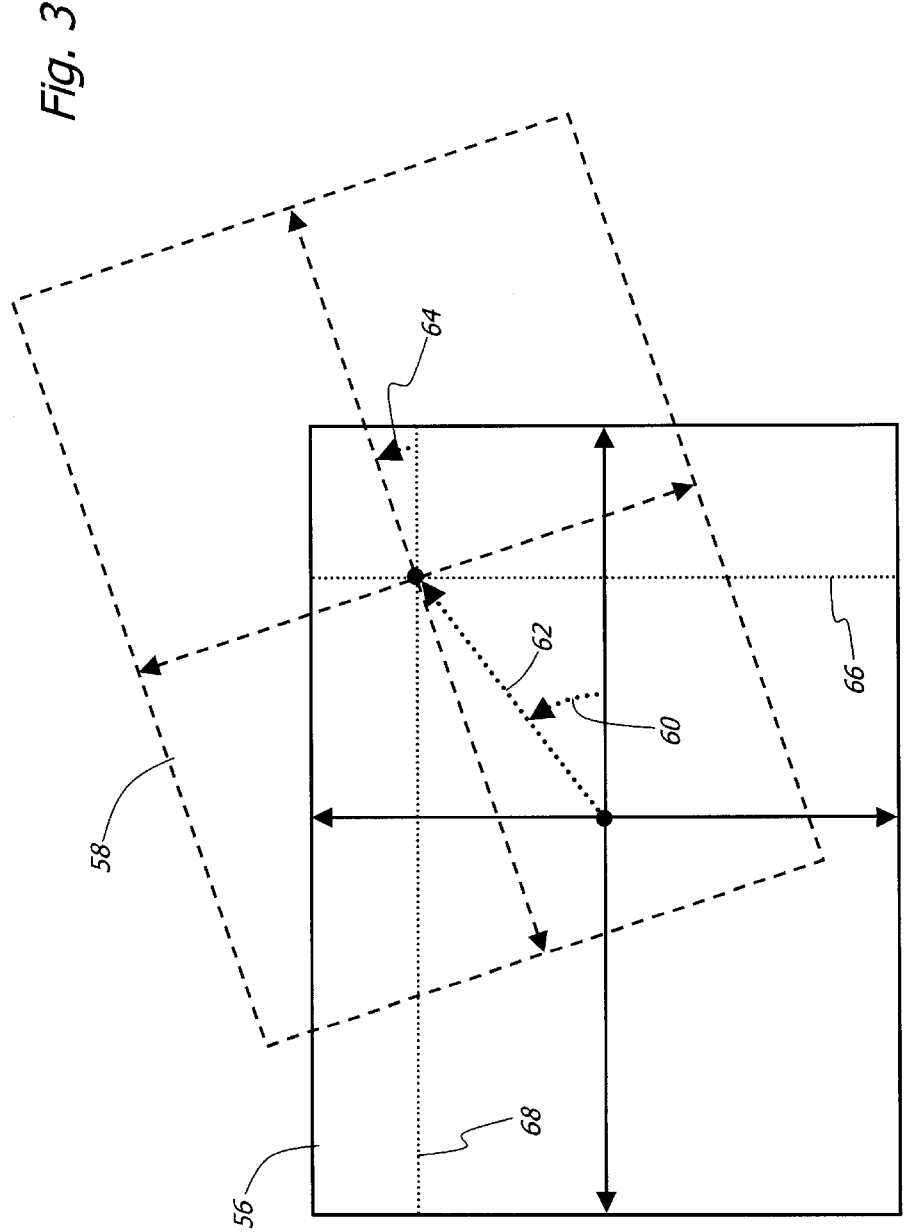
FIG. 3 is a diagram showing the view-frame mode of operation according to the preferred embodiment of the invention.

A second mode of operation, which can be thought of as view-frame mode, addresses this issue. As shown in FIG. 3, the control coordinate system for specifying adjustment is aligned with the center of the current view 56. The view-frame mode control coordinate system always moves with the view. The user specifies a desired view 58 based on the way in which the current view 56 appears on the screen. Through control of the joystick, the user may choose a direction and speed to move the center of the view and a rotation for the rotational view orientation. The interface then determines the best way to adjust the endoscope to achieve the desired view 58. View-frame mode is ideal for making small adjustments to the current view.

In controlling view-frame mode, joystick inputs must be converted to comprise a direction angle 60, a step distance angle 62, and a view rotation angle 64. The following variables are provided in the interface system for storing these angle values:

$\alpha_V$=stores the angle of the direction selected 60.

$\beta_V$=stores the angle of the step distance selected 62.

$\gamma_V$=stores the view rotation angle selected 64 minus the direction angle selected 60.

FIG. 3 shows how the joystick inputs are interpreted during view-frame operation. An X value 66 and a Y value 68 from the joystick together describe a center for the desired view 58. An inverse tangent function is used to calculate a value for $\alpha_V$. The Pythagorean Theorem is used to calculate a distance which is then converted into a value for $\beta_V$. The Z value from the joystick is the desired view rotation angle 64.

Rotation matrices are used by the central control unit 44 to calculate the desired endoscope configuration in the preferred embodiment of view-frame mode. The variables $\alpha_V$, $\beta_V$, and $\gamma_V$ are used in the rotation matrix of Equation 1, which describes the orientation of the desired view relative to the current view.

$$R(\alpha_V, \beta_V, \gamma_V) = \begin{bmatrix} \cos\alpha_V & -\sin\alpha_V & 0 \\ \sin\alpha_V & \cos\alpha_V & 0 \\ 0 & 0 & 1 \end{bmatrix} \begin{bmatrix} \cos\beta_V & 0 & \sin\beta_V \\ 0 & 1 & 0 \\ -\sin\beta_V & 0 & \cos\beta_V \end{bmatrix} \begin{bmatrix} \cos\gamma_V & -\sin\gamma_V & 0 \\ \sin\gamma_V & \cos\gamma_V & 0 \\ 0 & 0 & 1 \end{bmatrix} \quad \text{Equation 1}$$

The variables $\theta_C$, $\phi_C$, and $\zeta_C$ are used in the rotation matrix of Equation 2, which describes the orientation of the current view relative to the default position of the endoscope.

$$R(\theta_C, \phi_C, \zeta_C) = \begin{bmatrix} \cos\theta_C & -\sin\theta_C & 0 \\ \sin\theta_C & \cos\theta_C & 0 \\ 0 & 0 & 1 \end{bmatrix} \begin{bmatrix} \cos\phi_C & 0 & \sin\phi_C \\ 0 & 1 & 0 \\ -\sin\phi_C & 0 & \cos\phi_C \end{bmatrix} \begin{bmatrix} \cos\zeta_C & -\sin\zeta_C & 0 \\ \sin\zeta_C & \cos\zeta_C & 0 \\ 0 & 0 & 1 \end{bmatrix} \quad \text{Equation 2}$$

The rotation matrix of Equation 3 describes the orientation of the desired view relative to the default position of the endoscope.

$$R(\theta_D,\phi_D,\zeta_D) = R(\theta_C,\phi_C,\zeta_C) \cdot R(\alpha_V,\beta_V,\gamma_V) \quad \text{Equation 3}$$

The rotation matrix of Equation 3 can also be expressed as the rotation matrix of Equation 4, containing the desired endoscope configuration variables, $\theta_D$, $\phi_D$, and $\zeta_D$.

$$R(\theta_D, \phi_D, \zeta_D) = \begin{bmatrix} \cos\theta_D & -\sin\theta_D & 0 \\ \sin\theta_D & \cos\theta_D & 0 \\ 0 & 0 & 1 \end{bmatrix} \begin{bmatrix} \cos\phi_D & 0 & \sin\phi_D \\ 0 & 1 & 0 \\ -\sin\phi_D & 0 & \cos\phi_D \end{bmatrix} \begin{bmatrix} \cos\zeta_D & -\sin\zeta_D & 0 \\ \sin\zeta_D & \cos\zeta_D & 0 \\ 0 & 0 & 1 \end{bmatrix} \quad \text{Equation 4}$$

The rotation matrices of Equations 1–4 complete a transformation of the desired view coordinates from the current view coordinate system reference frame into the natural endoscope coordinate system reference frame.

In certain cases it may be preferable to operate while constrained to a coordinate system having longitude and latitude. This is often the case when significant view adjustments are required and the user desires to maintain a greater sense of the relative locations of features within the viewed cavity. Unfortunately, the natural endoscope coordinate system will not usually be aligned with the viewed cavity in a convenient manner. Therefore, a third mode of operation, which can be thought of as free-frame mode, is provided.

Figure 4:
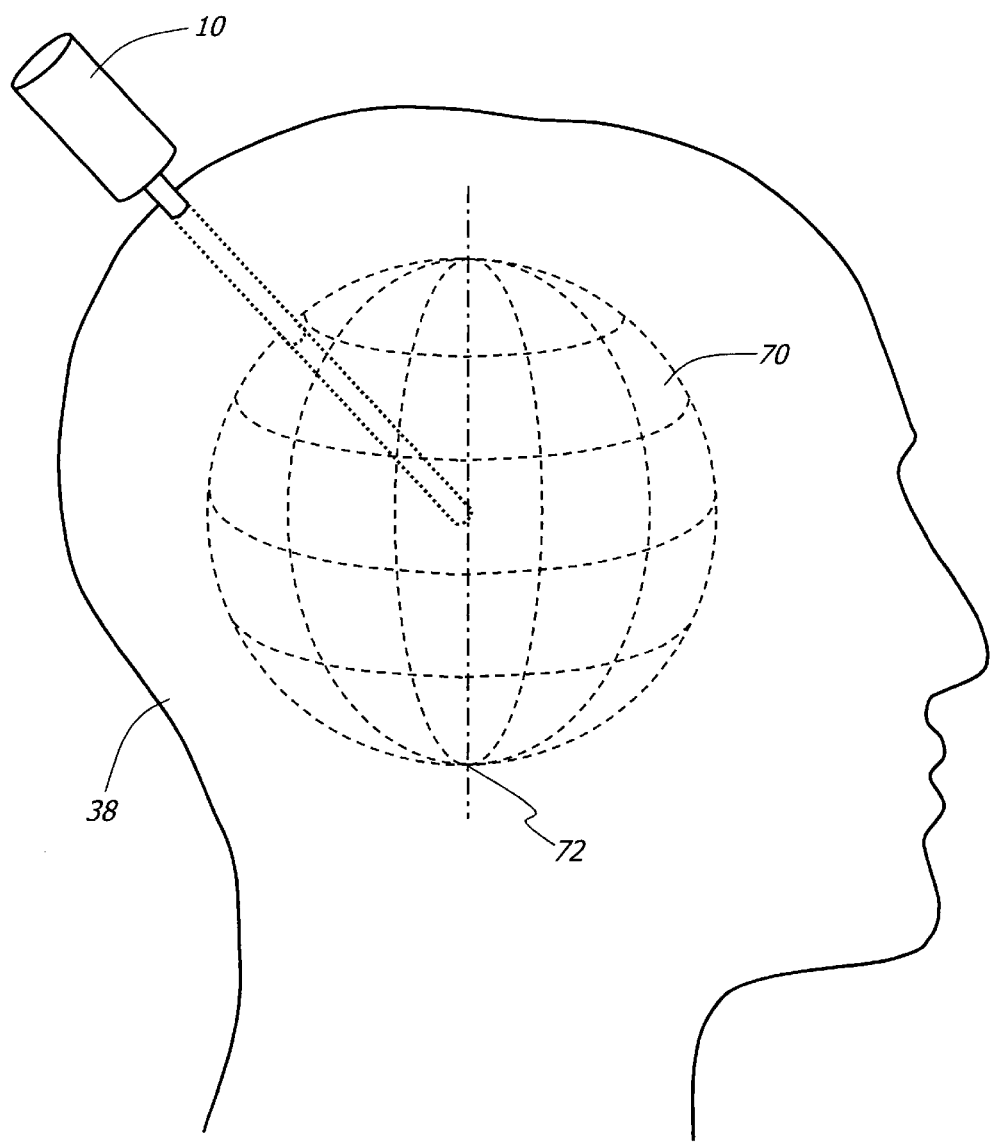
FIG. 4 is an illustration of an arbitrary coordinate system as defined by the free-frame mode of operation according to the preferred embodiment of the invention.

As shown in FIG. 4, the control coordinate system for specifying adjustment is aligned with an arbitrary coordinate system 70 defined within a cavity 38. The arbitrary coordinate system 70 may be aligned with gravity or with a particularly notable feature, and may be created automatically or based on a user's instructions. For example, the user may specify an orientation for an arbitrary coordinate system by selecting a direction to correspond with a pole of that arbitrary coordinate system. Alternatively, a coordinate system could be defined based on the output of an accelerometer responsive to gravity. The following variables are provided in the interface system for storing the orientation of an arbitrary coordinate system 70:

$\theta_F$=stores the encoder value describing the angle of the view vector about the longitudinal axis of the endoscope when the view is aligned at a pole of the arbitrary coordinate system 72.

$\phi_F$=stores the encoder value describing the angle of the view vector about the axis perpendicular to the longitudinal axis when the view is aligned at the pole of the arbitrary coordinate system 72.

$\zeta_F$=stores the encoder value describing the angle of the arbitrary rotational orientation of the view when the view is aligned at the pole of the arbitrary coordinate system 72.

In controlling free-frame mode, the view is defined and specified with respect to the arbitrary coordinate system. The following variables are provided in the interface system for storing the orientation of the view in an arbitrary coordinate system:

$\alpha_F$=stores the longitude value of the view vector in the arbitrary coordinate system.

$\beta_F$=stores the latitude value of the view vector in the arbitrary coordinate system.

$\gamma_F$=stores the angle of the arbitrary rotational orientation of the view in the arbitrary coordinate system.

Inputs from the user are directly applied to the orientation of the view within the arbitrary coordinate system. The X value from the joystick is used to increment $\alpha_F$. The Y value from the joystick is used to increment $\beta_F$. The Z value from the joystick may be used to increment $\gamma_F$. However, $\gamma_F$ is usually held constant in free-frame mode to simplify the use of the arbitrary coordinate system.

Rotation matrices are used by the central control unit 44 to calculate the desired endoscope configuration in the preferred embodiment of free-frame mode. The variables $\theta_F$, $\phi_F$, and $\zeta_F$ are used in Equation 5, which describes the orientation of the arbitrary coordinate system relative to the default position of the endoscope.

$$R(\theta_F, \phi_F, \zeta_F) = \begin{bmatrix} \cos\theta_F & -\sin\theta_F & 0 \\ \sin\theta_F & \cos\theta_F & 0 \\ 0 & 0 & 1 \end{bmatrix} \begin{bmatrix} \cos\phi_F & 0 & \sin\phi_F \\ 0 & 1 & 0 \\ -\sin\phi_F & 0 & \cos\phi_F \end{bmatrix} \begin{bmatrix} \cos\zeta_F & -\sin\zeta_F & 0 \\ \sin\zeta_F & \cos\zeta_F & 0 \\ 0 & 0 & 1 \end{bmatrix} \quad \text{Equation 5}$$

The variables $\alpha_F$, $\beta_F$, and $\gamma_F$ are used in Equation 6, which describes the orientation of the desired view within the arbitrary coordinate system.

$$R(\alpha_F, \beta_F, \gamma_F) = \begin{bmatrix} \cos\alpha_F & -\sin\alpha_F & 0 \\ \sin\alpha_F & \cos\alpha_F & 0 \\ 0 & 0 & 1 \end{bmatrix} \begin{bmatrix} \cos\beta_F & 0 & \sin\beta_F \\ 0 & 1 & 0 \\ -\sin\beta_F & 0 & \cos\beta_F \end{bmatrix} \begin{bmatrix} \cos\gamma_F & -\sin\gamma_F & 0 \\ \sin\gamma_F & \cos\gamma_F & 0 \\ 0 & 0 & 1 \end{bmatrix} \quad \text{Equation 6}$$

The rotation matrix of Equation 7 describes the orientation of the desired view relative to the default position of the endoscope.

$$R(\theta_D,\phi_D,\zeta_D) = R(\theta_F,\phi_F,\zeta_F) \cdot R(\alpha_F,\beta_F,\gamma_F) \quad \text{Equation 7}$$

The rotation matrix of Equation 7 can also be expressed as the rotation matrix of Equation 8, containing the desired endoscope configuration variables $\theta_D$, $\phi_D$, and $\zeta_D$.

$$R(\theta_D, \phi_D, \zeta_D) = \begin{bmatrix} \cos\theta_D & -\sin\theta_D & 0 \\ \sin\theta_D & \cos\theta_D & 0 \\ 0 & 0 & 1 \end{bmatrix} \begin{bmatrix} \cos\phi_D & 0 & \sin\phi_D \\ 0 & 1 & 0 \\ -\sin\phi_D & 0 & \cos\phi_D \end{bmatrix} \begin{bmatrix} \cos\zeta_D & -\sin\zeta_D & 0 \\ \sin\zeta_D & \cos\zeta_D & 0 \\ 0 & 0 & 1 \end{bmatrix} \quad \text{Equation 8}$$

The rotation matrices of Equations 5–8 complete a transformation of the desired view coordinate from the arbitrary coordinate system reference frame into the natural endoscope coordinate system reference frame.

Additional sets of free-frame variables in the interface system enable the user to store multiple arbitrary coordinate systems. These coordinate systems may be configured independently, each based on a different set of preferences. When switching into an arbitrary coordinate system, either from a different arbitrary coordinate system or from a different mode, the current view values for $\alpha_F$, $\phi_F$, and $\gamma_F$ are determined for the desired arbitrary coordinate system before that arbitrary coordinate system is used. The rotation matrix of Equation 9, an inverse of the rotation matrix of Equation 5, is needed to calculate $\alpha_F$, $\beta_F$, and $\gamma_F$.

$$R^{-1}(\theta_F, \phi_F, \zeta_F) = \begin{bmatrix} \cos\zeta_F & \sin\zeta_F & 0 \\ -\sin\zeta_F & \cos\zeta_F & 0 \\ 0 & 0 & 1 \end{bmatrix} \begin{bmatrix} \cos\phi_F & 0 & -\sin\phi_F \\ 0 & 1 & 0 \\ \sin\phi_F & 0 & \cos\phi_F \end{bmatrix} \begin{bmatrix} \cos\theta_F & \sin\theta_F & 0 \\ -\sin\theta_F & \cos\theta_F & 0 \\ 0 & 0 & 1 \end{bmatrix} \quad \text{Equation 9}$$

The rotation matrix of Equation 10 describes the orientation of the view within the arbitrary coordinate system.

$$R(\alpha_F,\beta_F,\gamma_F) = R^{-1}(\theta_F,\phi_F,\zeta_F) \cdot R(\theta_C,\phi_C,\zeta_C) \quad \text{Equation 10}$$

The rotation matrix of Equation 10 can also be expressed as the rotation matrix of Equation 11, containing the view orientation variables $\alpha_F$, $\beta_F$, and $\gamma_F$.

$$R(\alpha_F, \beta_F, \gamma_F) = \begin{bmatrix} \cos\alpha_F & -\sin\alpha_F & 0 \\ \sin\alpha_F & \cos\alpha_F & 0 \\ 0 & 0 & 1 \end{bmatrix} \quad \text{Equation 11}$$

-continued $$\begin{bmatrix} \cos\beta_F & 0 & \sin\beta_F \\ 0 & 1 & 0 \\ -\sin\beta_F & 0 & \cos\beta_F \end{bmatrix} \begin{bmatrix} \cos\gamma_F & -\sin\gamma_F & 0 \\ \sin\gamma_F & \cos\gamma_F & 0 \\ 0 & 0 & 1 \end{bmatrix}$$

The rotation matrices of Equations 9–11 complete a transformation of the current view coordinate from the natural endoscope coordinate system reference frame into the arbitrary coordinate system reference frame.

Memory is provided in the interface system for storing multiple sets of encoder variables. Each of the sets of encoder variables is a stored endoscope configuration. Each of the stored endoscope configurations corresponds to a view. The stored endoscope configurations enable the user to return to a previous view.

Figure 5:
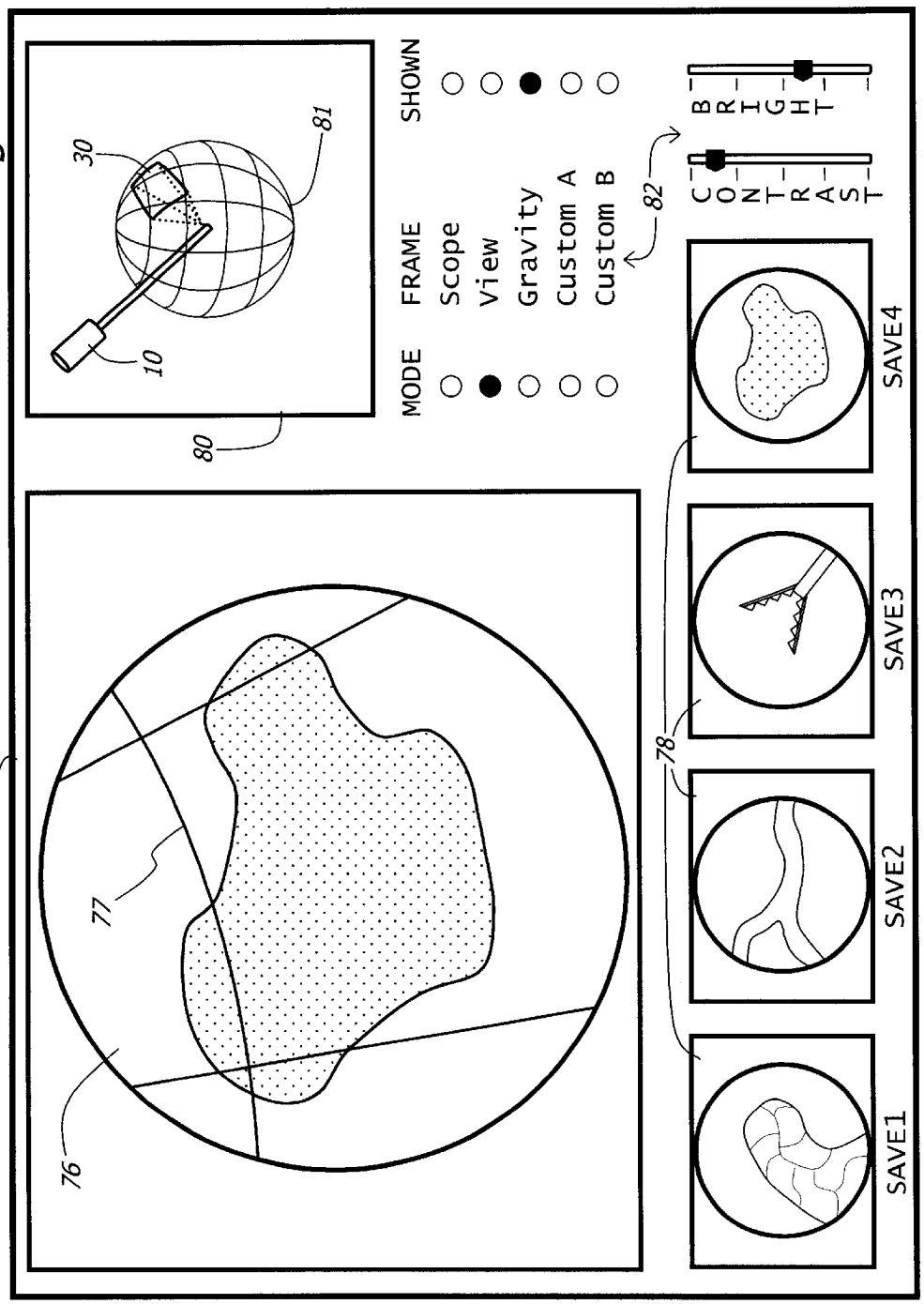
FIG. 5 is shows a displayed output from the endoscopic operating system according to the preferred embodiment of the invention.

The endoscopic video image and additional relevant information are presented to the user in a convenient fashion on a video display device. FIG. 5 illustrates an embodiment of this presentation. The screen of the display device 74 is organized into multiple sections, each with a different purpose. A large section of the screen 74 is used to display a video image 76 from the endoscope. A representation of a coordinate system 77 may be graphically superimposed on the video image 76 to aid the user in understanding and using that coordinate system. Several smaller captured images 78 are provided, each one corresponding to a stored endoscope configuration. The captured images 78 act in place of names to allow a user to easily identify each stored endoscope configuration. A computer generated depiction of the endoscope 80 is provided to assist the user in understanding the current view 30. The depiction 80 shows the endoscope 10 and the current view 30 from a viewpoint outside of the cavity. One or more coordinate systems 81 may also be shown in this depiction 80. Additionally, the depiction 80 may include simulated important features or other markings (not shown) to aid the situational understanding of the user. For example, a tumor to be removed, as located in a preoperative scan, could be shown in the depiction 80 to aid a surgeon in locating and identifying the tumor visually. In yet another section of the screen 74, the current mode and display settings 82 are displayed. In an alternative embodiment, the information discussed above may be displayed on multiple display devices. For example, the endoscopic image might be displayed separately from the other endoscopic operating system information.

FIG. 6A is a flow chart illustrating the operation of the central control unit 44, shown in FIG. 2, according to an embodiment of the invention. The central control unit 44 waits for a signal indicating user input 84. If it receives a joystick input 86, it prepares to perform the view adjustment desired by the user. The first step in achieving this adjustment is to identify the current operating mode of the interface system 88. The next step is to calculate values for the desired endoscope configuration variables $\theta_D$, $\phi_D$, and $\zeta_D$ in a manner corresponding to the current operating mode 90, 92, 94 as described above. These values are then sent to the motor controller unit 46, which appropriately moves the motors 96. Once this move has been completed, the interface system resets and waits for another input 84.

If the central control unit 44 receives a button input 98, it first identifies the type of button pressed 100. If the user has chosen to set a new mode 102, the mode is changed and the adjustment sequence is started 104. If the user has selected a stored endoscope configuration 106, the interface system instructs the endoscope to adjust directly to that endoscope configuration 96. If the user has elected to save the current endoscope configuration 108, the current endoscope configuration variables and current image are stored in memory before the interface system resets and waits for another input 84. If the user has chosen to adjust the interface settings 110, the appropriate adjustment is made, and the interface system resets and waits for another input 84.

Figure 6B:
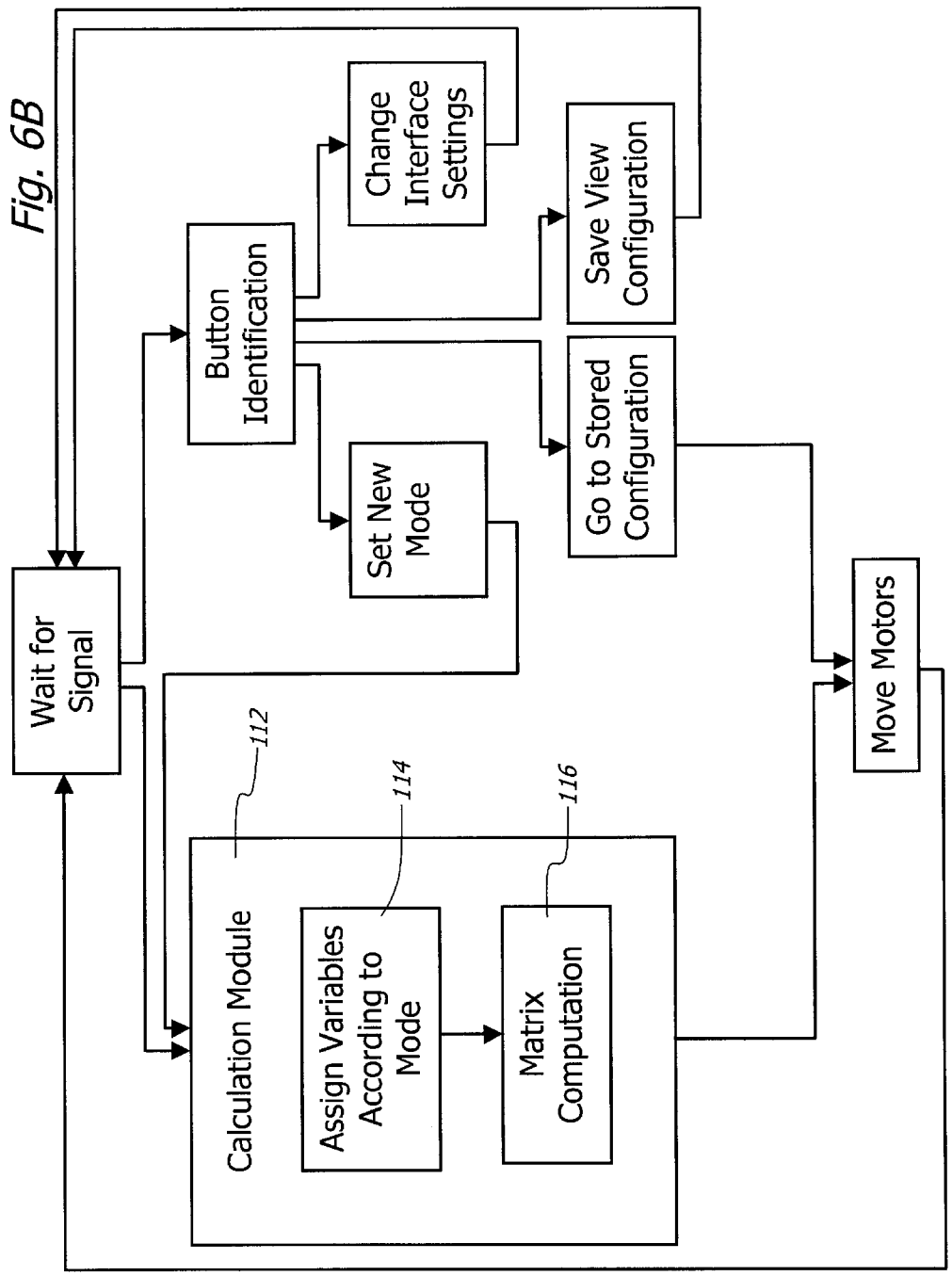

Even though the calculations required are specific to each mode of operation of the preferred embodiment, they are largely similar. Endoscope-frame mode can be simulated in free-frame mode by utilizing a coordinate system aligned with the natural coordinate system of the endoscope. This eliminates the need for a separate calculation method for endoscope-frame mode. View-frame mode and free-frame mode both involve a similar matrix multiplication. As shown in FIG. 6B, the program can therefore be simplified by combining the three modes into a single calculation module 112. When calculating an adjustment, values appropriate for the current mode are first assigned to variables 114. A generic matrix computation 116 can then be used to solve for the desired encoder values.

Accordingly, the present invention provides an interface for a variable direction of view endoscope that is easy to use and capable of adjusting multiple degrees of freedom of the endoscope simultaneously and precisely according to the desires of the user.

The present invention has been described above in terms of a presently preferred embodiment so that an understanding of the present invention can be conveyed. However, there are many alternative arrangements for an interface for a variable direction of view endoscope and methods of operation not specifically described herein but with which the present invention is applicable. For example, the display features of the preferred embodiment of the present invention could be used in a system that does not control the endoscope. Although specific formulas were given for an endoscope of the type shown in FIG. 1, the interface of the present invention could be applied to any type of variable direction of view endoscope when provided with calculation functions consistent with the operation of the endoscope selected. Some endoscope variations would utilize electronic processing and memory instead of motors and encoders to accomplish view adjustments. In addition, while the examples were given with respect to endoscopes for use in surgical procedures, the present invention would be equally applicable with respect to borescopes or the like for use within various mechanical structures. The scope of the present invention should therefore not be limited by the embodiments illustrated, but rather it should be understood that the present invention has wide applicability with respect to multi-directional viewing instruments and procedures generally. All modifications, variations, or equivalent elements and implementations that are within the scope of the appended claims should therefore be considered within the scope of the invention.

We claim:

1. A system for viewing the inside of a cavity using a variable direction of view endoscope, wherein a view vector is located at a distal end of said endoscope, and wherein said endoscope has a current endoscope configuration, comprising:

an input device that receives commands from a user;
a tracking device that provides view vector orientation information;
a processing device that receives said commands and said orientation information and performs operations comprising the calculation of a desired endoscope configuration based on said commands and said orientation information, wherein said commands are interpreted by said processing device with respect to a control coordinate system that can change in alignment with said endoscope;

a control device that adjusts said endoscope to make said current endoscope configuration equivalent to said desired endoscope configuration; and a display device that displays a current endoscopic view.

2. The system according to claim 1, wherein said control coordinate system adjusts in correspondence with said current endoscopic view, remaining stationary relative thereto.

3. The system according to claim 1, wherein said control coordinate system is aligned with a natural coordinate system of said endoscope.

4. The system according to claim 1, wherein said control coordinate system is aligned to a user specified orientation.

5. The system according to claim 1, wherein said control coordinate system is aligned with gravity.

6. The system according to claim 1, wherein one or more coordinate systems are displayed on said display device, superimposed on said current endoscopic view.

7. The system according to claim 1, further comprising a depiction of said endoscope.

8. The system according to claim 1, further comprising a depiction of said view vector.

9. The system according to claim 1, further comprising a depiction of one or more coordinate systems.

10. The system according to claim 1, further comprising a depiction of one or more features corresponding to the surroundings of the endoscope.

11. The system according to claim 1, wherein said processing device stores one or more endoscope configurations in a memory thereof.

12. The system according to claim 11, further comprising a display of one or more endoscopic images, each relating to a stored endoscope configuration.

13. A system for viewing the inside of a cavity using a variable direction of view endoscope, wherein a view vector is located at a distal end of said endoscope, and wherein said endoscope has a current endoscope configuration, comprising:

an input device that receives commands from a user;

a tracking device that provides view vector orientation information;

a processing device that receives said commands and said orientation information and performs operations comprising the calculation of a desired endoscope configuration based on said commands and said orientation information, wherein said commands are interpreted by said processing device with respect to a control coordinate system that can change in alignment with said endoscope, and wherein said endoscope becomes adjusted such that said current endoscope configuration is equivalent to said desired endoscope configuration; and a viewing device that provides a current endoscopic view.

14. A system for viewing the inside of a cavity using a variable direction of view endoscope, wherein a view vector is located at a distal end of said endoscope, and wherein said endoscope has a current endoscope configuration, comprising:

an input means for receiving commands from a user;

a tracking means for providing view vector orientation information;

a processing means for receiving said commands and said orientation information and for performing operations, comprising the calculation of a desired endoscope configuration based on said commands and said orientation information, wherein said commands are interpreted by said processing device with respect to a control coordinate system that can change in alignment with said endoscope;

an adjusting means for adjusting said endoscope to make said current endoscope configuration equivalent to said desired endoscope configuration; and a viewing means for providing a current endoscopic view.

15. An interface for use with a variable direction of view endoscope, wherein a distal portion of said endoscope is disposed within a cavity, comprising:

an input means for receiving commands from a user;

a tracking means for providing view vector orientation information;

a processing means for receiving said commands and said orientation information and performing operations, comprising the calculation of a coordinate system that can change in alignment with said endoscope; and a viewing means for providing a current endoscopic view.

16. The interface according to claim 15, wherein said coordinate system is configured based on operation characteristics and orientation of said endoscope.

17. The interface according to claim 15, wherein said coordinate system is configured based on the configuration of said endoscope, wherein said coordinate system adjusts in correspondence with said endoscopic view, remaining stationary relative thereto.

18. The interface according to claim 15, wherein said coordinate system is aligned to a user specified orientation.

19. The interface according to claim 15, wherein said coordinate system is aligned with gravity.

20. The interface according to claim 15, wherein lines representing said coordinate system are superimposed on said current view.

21. The interface according to claim 15, further comprising a depiction of said endoscope.

22. The interface according to claim 15, further comprising a depiction of said view vector.

23. The interface according to claim 15, further comprising a depiction of one or more coordinate systems.

24. The interface according to claim 15, further comprising a depiction of one or more features corresponding to the surroundings of the endoscope.

25. The interface according to claim 15, further comprising a plurality of prior view images.

* * * * *